(12) United States Patent
Zeng et al.

(10) Patent No.: US 11,952,356 B2
(45) Date of Patent: Apr. 9, 2024

(54) CRYSTALLINE FORM OF 1,4-BIS[1,2-BENZISOSELENAZOL-3(2H)-ONE]-BUTANE, METHOD FOR PREPARING SAME AND USE THEREOF

(71) Applicant: SHANGHAI YUANXI MEDICINE CORP., Shanghai (CN)

(72) Inventors: Huihui Zeng, Shanghai (CN); Hanwei Yin, Shanghai (CN)

(73) Assignee: SHANGHAI YUANXI MEDICINE CORP., Shanghai (CN)

( * ) Notice: Subject to any disclaimer, the term of this patent is extended or adjusted under 35 U.S.C. 154(b) by 12 days.

(21) Appl. No.: 17/596,601

(22) PCT Filed: Jan. 20, 2020

(86) PCT No.: PCT/CN2020/073280
§ 371 (c)(1),
(2) Date: Dec. 14, 2021

(87) PCT Pub. No.: WO2020/258882
PCT Pub. Date: Dec. 30, 2020

(65) Prior Publication Data
US 2022/0306594 A1 Sep. 29, 2022

(30) Foreign Application Priority Data
Jun. 24, 2019 (CN) .......................... 201910550238.4

(51) Int. Cl.
*C07D 293/12* (2006.01)

(52) U.S. Cl.
CPC ........ *C07D 293/12* (2013.01); *C07B 2200/13* (2013.01)

(58) Field of Classification Search
CPC .......................... C07D 293/12; C07D 293/10; C07B 2200/13; A61K 9/0053; A61K 9/08; A61K 9/10; A61K 47/38; A61K 31/41; A61P 1/16; A61P 9/00; A61P 17/16; A61P 19/02; A61P 31/00; A61P 31/20; A61P 35/00; A61P 37/02; A61P 1/02; A61P 11/00; A61P 17/00; A61P 29/00; A61P 31/12; A61P 37/00
(Continued)

(56) References Cited

U.S. PATENT DOCUMENTS

2005/0014801 A1   1/2005  Zeng

FOREIGN PATENT DOCUMENTS

CN   1511834 A   7/2004
CN   1704409 A   12/2005
(Continued)

OTHER PUBLICATIONS

He, Jie et al. "Inhibition of Thioredoxin Reductase by a Novel Series of Bis-1, 2-benzisoselenazol-3(2H)-ones: Organoselenium Compounds for Cancer Therapy", Bioorganic & Medicinal Chemistry, vol. 20, No. 12, Apr. 23, 2012, ISSN: 0968-0896.
(Continued)

*Primary Examiner* — Taylor V Oh
(74) *Attorney, Agent, or Firm* — NKL Law; Allen Xue

(57) ABSTRACT

A crystalline form I of 1,4-BIS[1,2-BENZISOSELENAZOL-3(2H)-one]-butane has characteristic peaks at 2θ angles of 6.17±0.20°, 12.28±0.20°, 18.44±0.20°, 25.92±0.20° and 30.95±0.20° by X-ray powder diffraction using Cu-Kα radiation.

16 Claims, 10 Drawing Sheets

Specification includes a Sequence Listing.

(58) Field of Classification Search
USPC .......................................................... 514/359
See application file for complete search history.

(56) References Cited

FOREIGN PATENT DOCUMENTS

| | | |
|---|---|---|
| CN | 101781283 A | 7/2010 |
| RU | 2324688 C2 | 5/2008 |

OTHER PUBLICATIONS

Zheng, Xiaoqing et al.; "Butaselen prevents hepatocarcinogenesis and progression through inhibiting thioredoxin reductase activity"; Redox Biology; vol. 14, 2018; available online Sep. 22, 2017; pp. 237-249.

Caira, Mino R.; "Crystalline Polymorphism of Organic Compounds"; Design of Organic Solids; Topics in Current Chemistry, vol. 198; Year: 1998; pp. 164-208, Springer, Berlin, Heidelberg.

CRYSTALLINE FORM OF 1,4-BIS[1,2-BENZISOSELENAZOL-3(2H)-ONE]-BUTANE, METHOD FOR PREPARING SAME AND USE THEREOF

CROSS-REFERENCE TO RELATED APPLICATIONS

This application is a U.S. national stage entry of PCT International Application No. PCT/CN2020/073280, filed Jan. 20, 2020, which claims the priority to Chinese Patent Application No. 201910550238.4, entitled "CRYSTALLINE FORM OF 1,4-BIS[1,2-BENZISOSELENAZOL-3(2H)-ONE]-BUTANE, METHOD FOR PREPARING SAME AND USE THEREOF" and filed on Jun. 24, 2019, with China National Intellectual Property Administration, the content of which is incorporated herein by reference in its entirety.

INCORPORATION OF SEQUENCE LISTING

This application contains a sequence listing submitted in Computer Readable Form (CRF). The CFR file containing the sequence listing entitled "PA150-0134_ST25.txt", which was created on Dec. 14, 2021, and is 1,662 bytes in size. The information in the sequence listing is incorporated herein by reference in its entirety.

TECHNICAL FIELD

The present invention relates to the field of crystalline form preparation, and particularly to a crystalline form of 1,4-BIS[1,2-BENZISOSELENAZOL-3(2H)-one]-butane, a method for preparing the same and use thereof.

BACKGROUND

The structure of 1,4-BIS[1,2-BENZISOSELENAZOL-3(2H)-one]-butane is shown below:

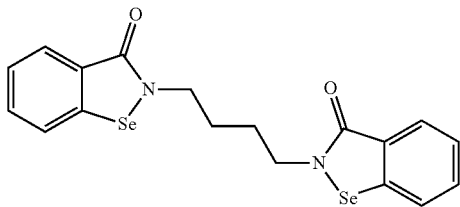 [SMILES: O=c1c2ccccc2[se]n1CCCCn1[se]c2ccccc2c1=O]

The compound is widely used, for example: 1) in preparing medicaments for pre-treating various fibrosis diseases, such as hepatic fibrosis, pulmonary fibrosis, renal fibrosis, myelofibrosis, skin fibrosis, cystic fibrosis, oral submucous fibrosis or myocardial fibrosis; 2) in preparing cosmetics for treating skin fibrosis; 3) in preparing medicaments for preventing and treating arthritis, such as medicaments for preventing and treating rheumarthritis, rheumatoid arthritis, etc.; 4) in preparing medicaments for preventing and treating inflammations, such as medicaments for preventing and treating periodontitis, scapulohumeral periarthritis or myocarditis; 5) in preparing medicaments for treating various inflammatory diseases with fibrosis; 6) in preparing medicaments for preventing and treating tumor metastasis.

In the R&D process of medicaments, studies on crystalline forms play a vital role. Solid forms of a drug may have remarkable differences in aspects of appearance, solubility, melting point, dissolution rate, bioavailability and the like, thus influencing the stability, bioavailability and efficacy of the drug. Polymorphism of the drug is an important factor that influences the quality and clinical efficacy of the drug. Therefore, developing a pure, stable crystalline form is crucial for manufacture and application of a drug.

SUMMARY

To solve the technical problems described above, the present invention firstly provides a crystalline form I of 1,4-BIS[1,2-BENZISOSELENAZOL-3(2H)-one]-butane having characteristic peaks at 2θ angles of 6.15±0.20°, 12.28±0.20°, 18.44±0.20°, 25.92±0.20° and 30.95±0.20° by X-ray powder diffraction using Cu-Kα radiation.

According to an embodiment of the present invention, the crystalline form I has characteristic peaks at 2θ angles of 6.15±0.20°, 12.28±0.20°, 18.44±0.20°, 19.09±0.20°, 22.20±0.20°, 23.68±0.20°, 25.92±0.20°, 30.95±0.20° and 32.45±0.20° by X-ray powder diffraction using Cu-Kα radiation.

According to an embodiment of the present invention, the crystalline form I has characteristic peaks at 2θ angles of 6.15±0.20°, 12.28±0.20°, 18.44±0.20°, 19.09±0.20°, 21.89±0.20°, 22.20±0.20°, 23.68±0.20°, 25.92±0.20°, 27.50±0.20°, 30.95±0.20°, 32.45±0.20°, 35.79±0.20°, 37.37±0.20° and 37.72±0.20° by X-ray powder diffraction using Cu-Kα radiation.

According to an embodiment of the present invention, the crystalline form I has the following characteristic peaks in 2θ angle and relative intensities by X-ray powder diffraction using Cu-Kα radiation:

| 2θ | I % |
| --- | --- |
| 6.147 | 14.3 |
| 11.07 | 0.1 |
| 12.276 | 100 |
| 14.949 | 0.5 |
| 15.371 | 0.4 |
| 16.901 | 0.6 |
| 18.053 | 0.9 |
| 18.441 | 9.3 |
| 19.091 | 4 |
| 19.565 | 0.2 |

| 2-Theta | I % |
| --- | --- |
| 20.215 | 1.5 |
| 20.572 | 1.7 |
| 20.804 | 0.8 |
| 21.888 | 2.9 |
| 22.201 | 3.1 |
| 22.599 | 1.3 |
| 23.678 | 3.3 |
| 24.806 | 0.5 |
| 25.315 | 0.2 |
| 25.924 | 8.4 |
| 26.301 | 0.8 |
| 27.503 | 2.6 |
| 30.949 | 16.2 |
| 32.447 | 5.7 |
| 34.15 | 0.2 |
| 35.159 | 0.1 |
| 35.792 | 2.4 |
| 36.342 | 2 |
| 37.367 | 2.7 |
| 37.723 | 2.4 |
| 38.471 | 1.5 |

According to an embodiment of the present invention, the crystalline form I has an XRD pattern as substantially shown in FIG. 1.

According to an embodiment of the present invention, the crystalline form I has a DSC-TGA pattern as substantially shown in FIG. 2.

According to an embodiment of the present invention, the crystalline form I is a monocrystal having the following monocrystalline properties,

| | |
|---|---|
| T(K) | 298 |
| System | monoclinic |
| Space group | P21/a |
| Crystal size | 0.01 × 0.20 × 0.60 mm |
| a (Å) | 12.000 (1) |
| b (Å) | 4.921 (1) |
| c (Å) | 14.591 (1) |
| β (°) | 97.61 (1) |
| Volume of crystal cell V (Å$^3$) | 854.0 (1) |
| Z | 2 |
| Color | colorless |
| Shape | sheet |
| Density (g/cm$^3$) | 1.751 |
| Diffractometer | MAC DIP-203 OK |
| Radiation | MoKα |
| θRange | 0-180° |
| Rf | 0.043 |
| $R_w = (w = 11/\sigma|F|^2)$ | 0.044 |

The present invention further provides a method for preparing the crystalline form I as described above, comprising:
dissolving 1,4-BIS[1,2-BENZISOSELENAZOL-3(2H)-one]-butane in a solvent S1, and adding an antisolvent S2 to give the crystalline form I;
wherein the solvent S1 is selected from DMSO and a mixture of 1-10% acetone or tetrahydrofuran (v/v) in DMSO;
the solvent S2 is selected from water, acetonitrile, MTBE, isopropyl acetate, methanol and ethyl acetate, provided that when the solvent S1 is DMSO, the solvent S2 is not ethyl acetate.

According to an embodiment of the present invention, the volume ratio of the solvent S1 to the solvent S2 is 1:0.5-1:2, preferably 1:2 or 2:1.

According to an embodiment of the present invention, the crystallization procedure is preferably performed at 30-70° C., and more preferably at 40-60° C.

The present invention further provides use of the crystalline form I as described above in preparing a medicament or a cosmetic for inhibiting activities of gelatinase-2 and the gelatinase-9, or a medicament for treating an immune injury disease and an immune regulation function-dependent or -promoted relevant disease.

According to an embodiment of the present invention, the immune injury disease and the immune regulation function-dependent or -promoted relevant disease are selected from infection, viral hepatitis, allergic diseases, autoimmune diseases and acquired immunodeficiency syndrome.

According to an embodiment of the present invention, the medicament for inhibiting activities of gelatinase-2 and gelatinase-9 is selected from medicaments for preventing and treating fibrosis-related diseases, treating inflammation-related diseases, treating fibrosis-related complications with inflammation, or treating tumor metastases.

According to a preferred embodiment of the present invention, the fibrosis disease is selected from hepatic fibrosis, pulmonary fibrosis, renal fibrosis, myelofibrosis, skin fibrosis, cystic fibrosis, oral submucous fibrosis and myocardial fibrosis.

According to a preferred embodiment of the present invention, the inflammation-related disease is selected from hepatitis B, periodontitis, rheumarthritis, rheumatoid arthritis, scapulohumeral periarthritis and myocarditis.

According to a preferred embodiment of the present invention, the crystalline form I is used for preparing a medicament for treating hepatitis B or liver cancer.

According to an embodiment of the present invention, the hepatitis B is chronic adult hepatitis B with active virus replication, persistent elevated serum alanine aminotransferase (ALT) or histological active lesions in liver, or chronic hepatitis B virus (HBV) infection-compensated liver disease in children.

According to a preferred embodiment of the present invention, the liver cancer is HBV-associated liver cancer, or particularly, liver cancer with HBV.

The present invention further provides a pharmaceutical composition comprising the crystalline form I as described above.

The present invention further provides the pharmaceutical composition as described above for inhibiting activities of gelatinase-2 and gelatinase-9, or for treating an immune injury disease and an immune regulation function-dependent or -promoted relevant disease.

Beneficial Effects

The present invention provides a crystalline form I of the 1,4-BIS[1,2-BENZISOSELENAZOL-3(2H)-one]-butane. The crystalline form I has good stability, is not susceptible to polymorphic transition, is beneficial to the preparation, use, shipping and preservation of pharmaceutical compositions and preparations, and fully ensures the safety of medication and the quality of medicaments.

In addition, the crystalline form features high solubility, reasonable bioavailability, low toxicity and excellent tumor inhibitory activity. The inventors surprisingly found that the crystalline form I has good inhibitory activity against liver cancer, particularly HBV-associated liver cancer. As 80% of liver cancer patients in China are HBV carriers, the application of the crystalline form of the compound in liver cancer treatment has reasonable pertinence.

Finally, the preparation method of the crystalline form I features the advantages of ease-to-operate, good reproducibility, high yield and suitability for industrial production, thus having great application value.

DETAILED DESCRIPTION

Figure 1:
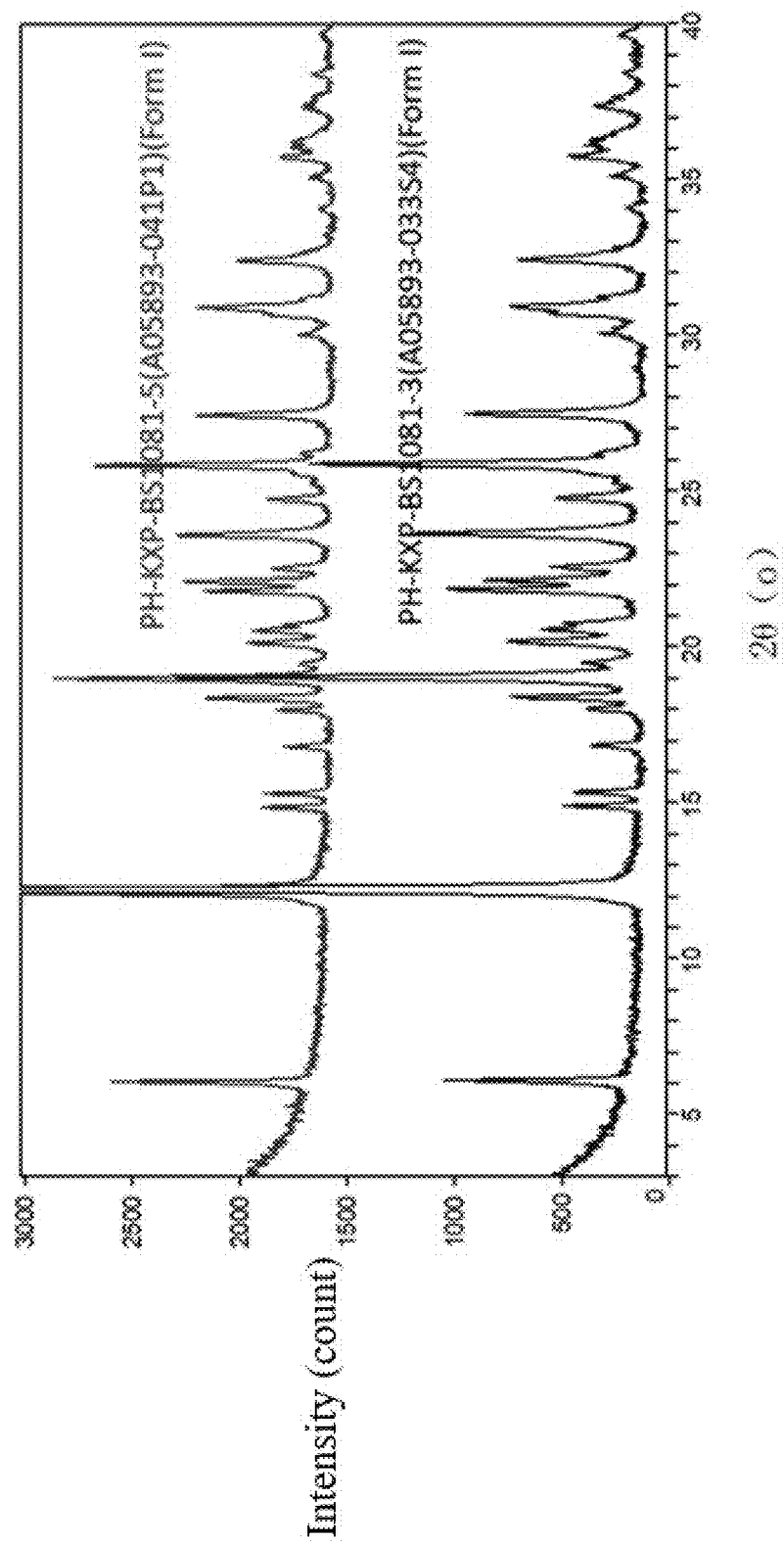
FIG. 1 illustrates an XRD pattern of the crystalline form I (FIG. 1 shows the results for two batches of the crystalline form I).

The technical scheme of the present invention will be further illustrated in detail with reference to the following specific examples. It should be understood that the following examples are merely exemplary illustration and explanation of the present invention, and should not be construed as limiting the protection scope of the present invention. All techniques implemented based on the aforementioned contents of the present invention are encompassed within the protection scope of the present invention.

Unless otherwise specified, the starting materials and reagents used in the following examples are all commercially available products or can be prepared by known methods.

X-ray powder diffraction (XRD) was performed with a D8 Advance X-ray powder diffractometer (Bruker) and a D2 Phaser X-ray powder diffractometer (Bruker). The platforms were equipped with a LynxEye detector. The X-ray powder diffractometer (Bruker) tested samples at 2θ scan angles from 3° to 40° with a step of 0.02°. The light tube voltage and current for testing were 40 kV and 40 mA, respectively.

The thermogravimetric analyzer was TGA Q500 or Discovery TGA 55 (TA, USA). The samples were placed in an equilibrated open aluminum sample tray and the weight was automatically measured in a TGA furnace. The samples were heated at a rate of 10° C./min to the final temperature. The differential scanning calorimeter was DSC Q200 or Discovery DSC 250 (TA, USA). The samples were accurately weighed and placed in a DSC sample tray with a pinhole, and the exact weights of the samples were recorded. The samples were heated at a ramp rate of 10° C./min to the final temperature.

Preparation Example 1. Preparation of 1,4-BIS[1,2-BENZISOSELENAZOL-3(2H)-one]-butane

1.1 Preparation of 2,2'-diselenibis(benzoic acid)

(1) Preparation of diazonium 2-chlorobenzoate 4.0 g of anthranilic acid was mixed with 40 mL of hydrochloric acid in a volume ratio of 1:1. The system was stirred in ice bath to keep the temperature below 5° C., then slowly and dropwise added to a solution of sodium nitrite (25 g) in water (20 mL), and incubated for 2 h to give diazonium 2-chlorobenzoate. The product was used directly in the next step without purification.

(2) 120 mL of water was added with 12 g of selenium powder and sodium hydroxide, slowly added with 10 g of sodium hydrosulfite under stirring, and incubated for 2 h to give a sodium diselenide solution. The solution was used directly in the next step without purification.

(3) the diazonium 2-chlorobenzoate solution obtained in step (1) was dropwise added into the sodium diselenide solution obtained in the step (2) under stirring, and the mixture was continuously stirred for 4 h until generated nitrogen was completely exhausted. The reaction mixture was acidified by hydrochloric acid, filtered to remove precipitates, washed with water, and dried in a desiccator to give 2,2'-diselenibis(benzoic acid). Melting point of the product after crystallization was 294° C.

$^1$-NMR (300 MHz, DMSO-$d_6$) δ: 7.33-8.04 (m, 4H, ph-H) 13.6 (br, COOH);
IR(KBr) $cm^{-1}$: (O—H) 3005, ($CO_2$) 1672, (C—N) 1264, C═C(phenyl ring) 1560, 1460,1417; MS-FAB (m/z): 201 [1/2$M^+$]

1.2 Preparation of 2-(chloroseleno)benzoyl Chloride 2,2'-diselenibis(benzoic acid) (40.0 g), 200 mL of thionyl chloride and DMF were stirred at reflux for 3 h, and subjected to rotary evaporation to remove excessive thionyl chloride. The residues were recrystallized in n-hexane to give 2-(chloroseleno)benzoyl chloride with melting point of 66° C.

$^1$H-NMR (300 MHz, DMSO-$d_6$) δ: 7.33-8.16 (m, 4H, ph-H).

1.3 Preparation of 1,4-bis[1,2-benzisoselenazol-3(2H)-one]-butane 3 mL of 1,4-butanediamine was dissolved in 50 mL of THF and added with triethylamine in ice bath and $N_2$ atmosphere. 2.9 g of 2-(chloroseleno)benzoyl chloride was dissolved in 60 mL of THF, and slwly and dropwise added with a 1,4-butanediamine solution to give a yellow solid. After the addition, the solution was heated to room temperature and reacted for 2 h. The solid was filtered, and washed with solvent, ethanol and diethyl ether several times. The product was recrystallized in DMSO-water to give 2 g of a pale yellow solid, m.p. 243-248° C.

$^1$H-NMR: (300 MHz, DMSO-d6) δ 7.37-8.04 (m, 4H, Ph-H), 3.75 (s, 2H, $CH_2$),1.64 (s, 2H, $CH_2$);
MS-FAB (m/z): 451 $[M]^+$.

Example 1. Preparation of Crystalline Form I 1,4-BIS[1,2-BENZISOSELENAZOL-3(2H)-one]-butane prepared in Preparation Example 1 was dissolved in a solvent, and an antisolvent was added to give the crystalline form I. The volumes of the used solvent and antisolvent are shown in the following table:

| Operating temperature | Solvent | Antisolvent | $V_{solvent}:V_{antisolvent}$ | Initial state | Product |
|---|---|---|---|---|---|
| 50° C. | DMSO | Water | 1:1 | Turbid | Crystalline form I |
| 50° C. | DMSO | Acetonitrile | 1:2 | Turbid | Crystalline form I |
| 50° C. | DMSO | MTBE | 1:2 | Turbid | Crystalline form I |

-continued

| Operating temperature | Solvent | Antisolvent | $V_{solvent}:V_{antisolvent}$ | Initial state | Product |
|---|---|---|---|---|---|
| 50° C. | DMSO | Isopropyl acetate | 1:2 | Clarified | Crystalline form I |
| 50° C. | DMSO | Methanol | 1:2 | Turbid | Crystalline form I |
| 50° C. | 10% acetone/DMSO | Water | 2:1 | Turbid | Crystalline form I |
| 50° C. | 10% acetone/DMSO | Acetonitrile | 1:2 | Turbid | Crystalline form I |
| 50° C. | 10% acetone/DMSO | Ethyl acetate | 1:2 | Clarified | Crystalline form I |
| 50° C. | 10% tetrahydrofuran/DMSO | Water | 2:1 | Turbid | Crystalline form I |
| 50° C. | 10% tetrahydrofuran/DMSO | Ethyl acetate | 1:2 | Clarified | Crystalline form I |

Figure 2:
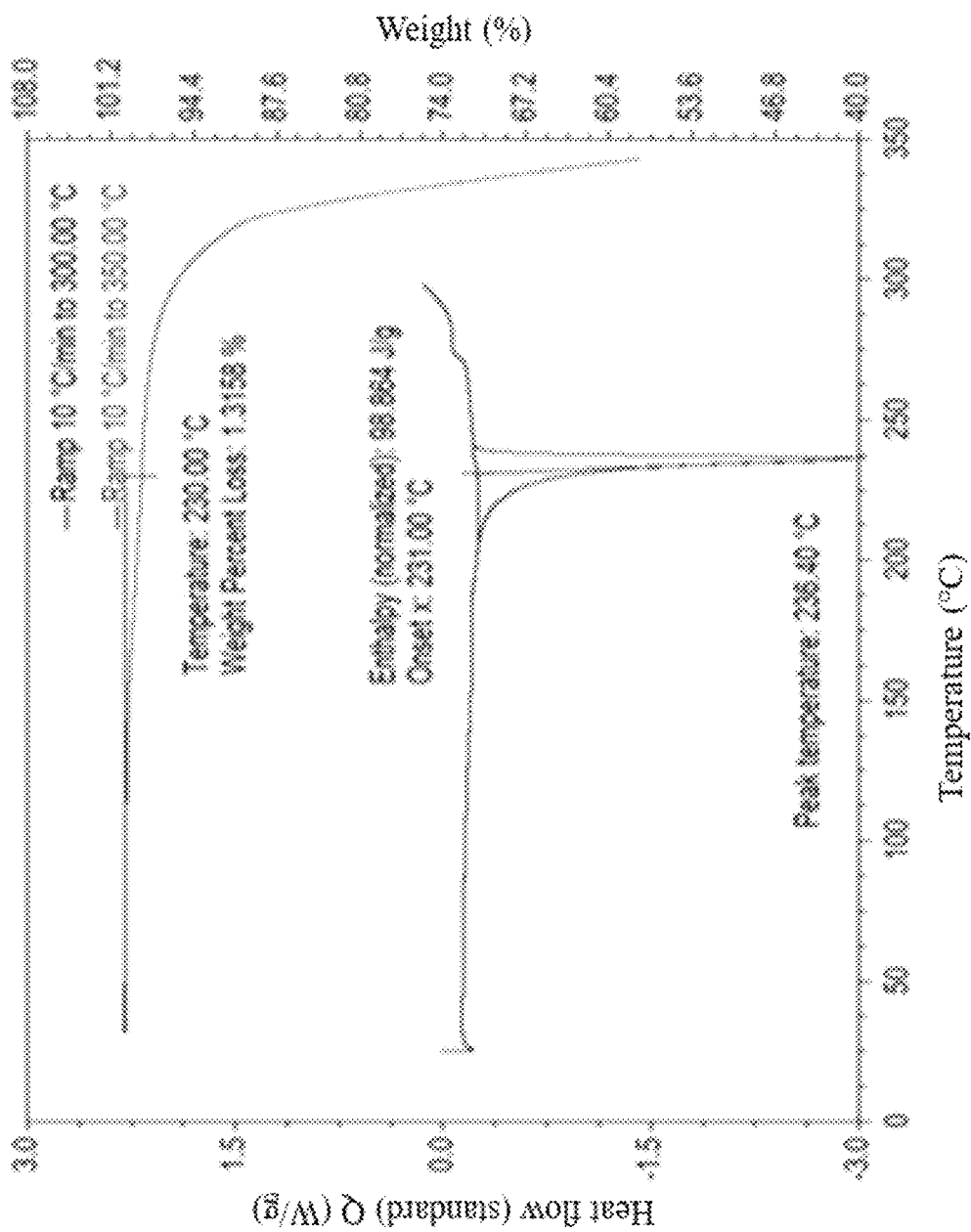
FIG. 2 illustrates a DSC-TGA pattern of the crystalline form I.

The XRD pattern of the crystalline form I is shown in FIG. 1. The DSC-TGA pattern is shown in FIG. 2.

Figure 5:
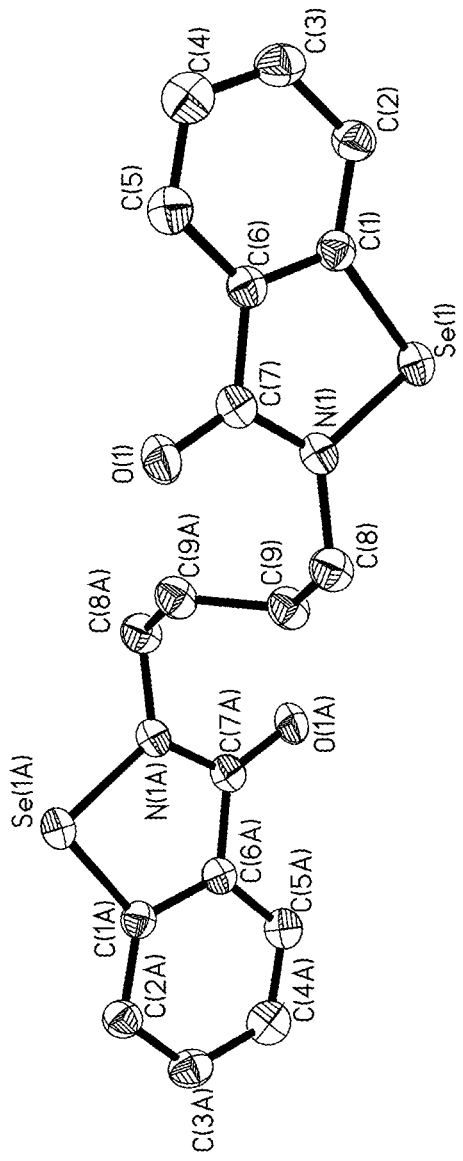
FIG. 5 illustrates the monocrystalline structure of the crystalline form I.

Further tests showed that the crystalline form I is a monocrystal as shown in FIG. 5, and the monocrystalline properties are as follows:

| | |
|---|---|
| T(K) | 298 |
| System | monoclinic |
| Space group | P21/a |
| Crystal size | 0.01 × 0.20 × 0.60 mm |
| a (Å) | 12.000 (1) |
| b (Å) | 4.921 (1) |
| c (Å) | 14.591 (1) |
| β (°) | 97.61 (1) |
| Volume of crystal cell V (Å$^3$) | 854.0 (1) |
| Z | 2 |
| Color | colorless |
| Shape | sheet |
| Density (g/cm$^3$) | 1.751 |
| Diffractometer | MAC DIP-203 OK |
| Radiation | MoKα |
| θRange | 0-180° |
| $R_f$ | 0.043 |
| $R_w = (w = 1/\sigma|F|^2)$ | 0.044 |

Comparative Example 1

Figure 3:
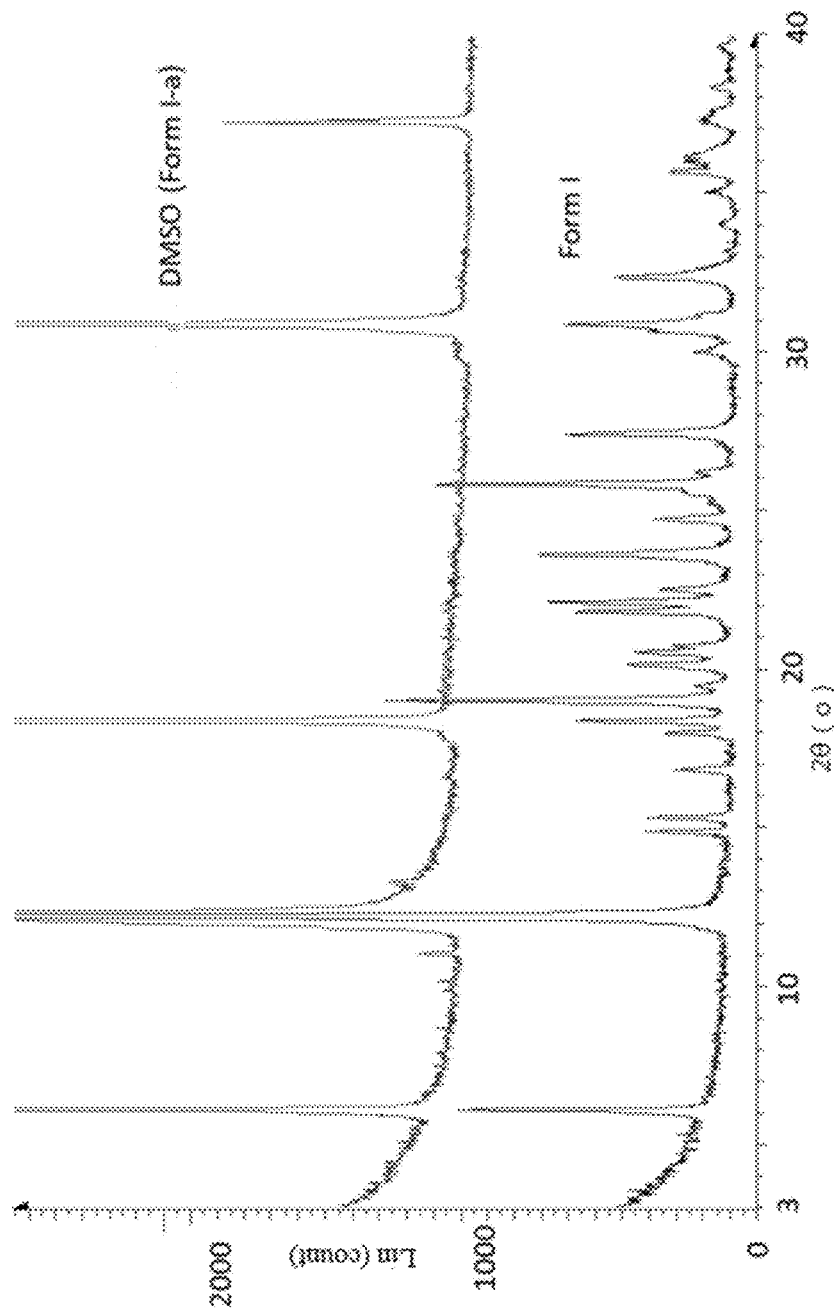
FIG. 3 illustrates XRD patterns of a crystalline form I-a and the crystalline form I.

1,4-BIS[1,2-BENZISOSELENAZOL-3(2H)-one]-butane prepared in Preparation Example 1 was dissolved in DMSO, and the solvent was evaporated to give a crystalline form I-a, of which the XRD pattern is shown in FIG. 3.

Comparative Example 2

1,4-BIS[1,2-BENZISOSELENAZOL-3(2H)-one]-butane prepared in Preparation Example 1 was dissolved in a good solvent DMSO, and added with an antisolvent butanone, ethanol or ethyl acetate (the volume ratio of the good solvent to the antisolvent was 1:2). All the antisolvents gave the crystalline form I-a.

Comparative Example 3

1,4-BIS[1,2-BENZISOSELENAZOL-3(2H)-one]-butane prepared in Preparation Example 1 was dissolved in a good solvent (10% acetone/DMSO or 10% tetrahydrofuran/DMSO), and added with an antisolvent ethanol (the volume ratio of the good solvent to the antisolvent was 1:2). Both good solvents gave the crystalline form I-a.

Figure 4:
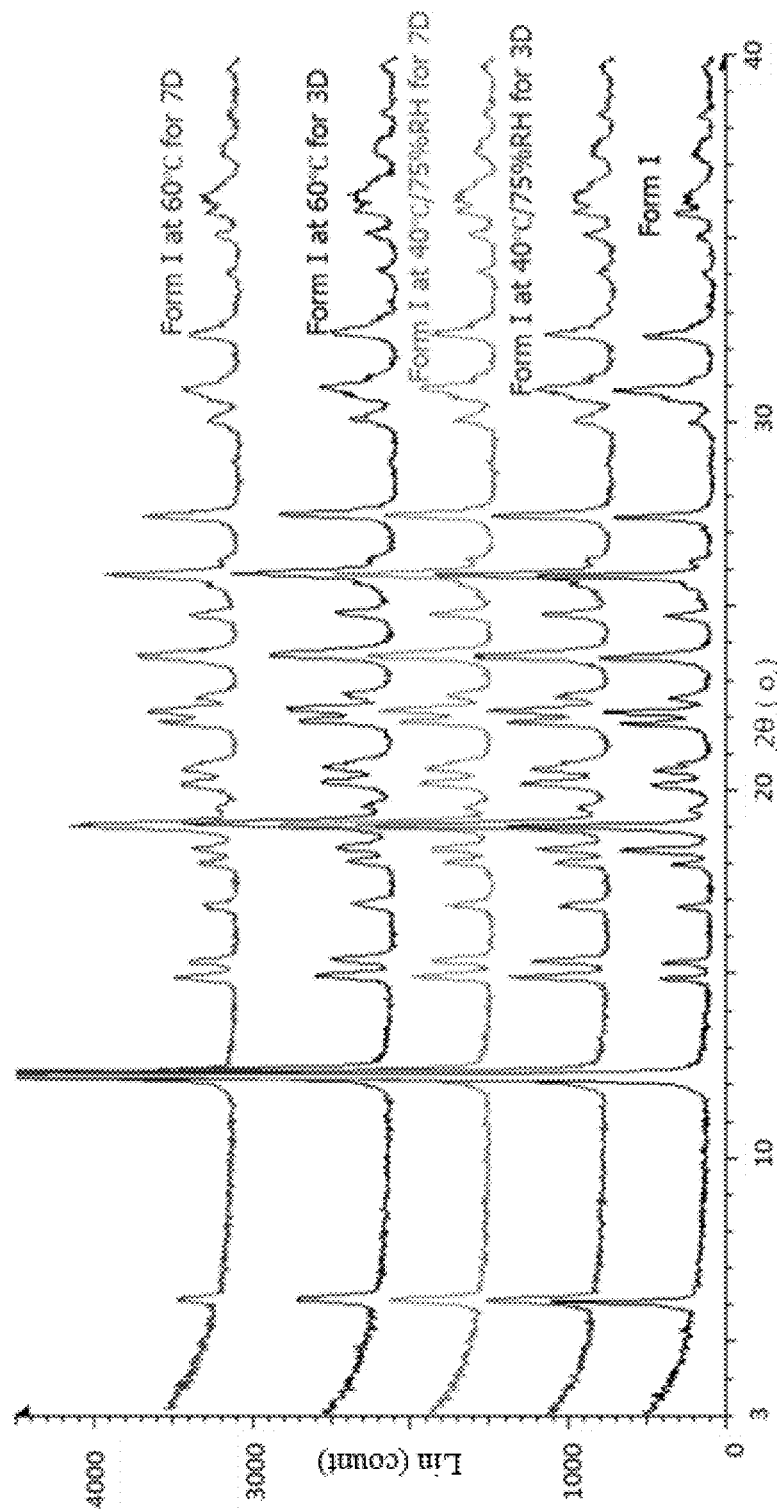
FIG. 4 illustrates XRD patterns of the crystalline form I after standing under various conditions.

Test Example 1. Stability Test of Crystalline Form I (1) Stability test was performed on crystalline form I prepared in Example 1. Procedures: Samples of the crystalline form I were placed into a stability test chamber for 3 to 7 days at 40° C./75% relative humidity and 60° C. The results are shown in FIG. 4. As can be seen from FIG. 4, the XRD pattern of the crystalline form I was unchanged after it was stored under different conditions, which demonstrates that the crystalline form I is stable in high temperature and high humidity conditions and has good stability.

(2) The crystalline form I-a prepared in Comparative Examples 1-3 was ground. By XRD it was determined that the powder was crystalline form I. As such, the crystalline form I is confirmed as the stable crystalline form of the 1,4-BIS[1,2-BENZISOSELENAZOL-3(2H)-one]-butane.

| Sample | Before grinding | After grinding |
|---|---|---|
| Example 1 | Crystalline form I | Crystalline form I |
| Comparative Example 1 | Crystalline form I-a | Crystalline form I |
| Comparative Example 2 | Crystalline form I-a | Crystalline form I |
| Comparative Example 3 | Crystalline form I-a | Crystalline form I |

In summary, the crystalline form I has good stability, is not susceptible to polymorphic transition, is beneficial to the preparation, use, shipping and preservation of pharmaceutical compositions and preparations, and fully ensures the safety of medication and the quality of medicaments.

Test Example 2. Tumor Inhibitory Activity Assay of Crystalline Form I in H22 Mice Crystalline form I was administered at a dose of 180 mg/kg: 180 mg of the crystalline form I was dissolved in 5 mL of 5‰ CMC-Na solution to give a suspension, which was administered at a dose of 5 mL/kg.

Procedures: A blank control group (5‰ CMC-Na, once daily, oral gavage) and a crystalline form I group (180 mg/kg, once daily, oral gavage) were set. After 2 days of acclimation, qualified animals were randomized into 4 groups with 10 animals each. On day 0, H22 cells were grafted at $1 \times 10^4$/mouse subcutaneously at the right axilla. The treatment started at 24 h after grafting. Long and short diameters of tumor were recorded daily and the tumor size was calculated according to the formula: long diameter× short diameter$^2$×0.5236. The body weight was measured every 2 days. After 21 days of treatment, blood was collected from eyeballs after chloral hydrate anesthesia. The mice were sacrificed and tumors were collected quickly. At the end of the experiment, tumors were weighed for summary, with relevant data statistics given in the following table:

Tumor growth inhibition by crystalline form I in H22 mouse (n=10)

| Day(s) | Crystalline form I group (%) |
|---|---|
| 9 | 70.42 |
| 10 | 78.32 |
| 11 | 76.31 |
| 12 | 78.27 |
| 13 | 76.03 |
| 14 | 72.24 |
| 15 | 65.74 |
| 16 | 76.97 |
| 17 | 78.21 |
| 18 | 82.33 |
| 19 | 87.15 |
| 20 | 88.49 |
| 21 | 86.67 |

| Group | Mean tumor weight (mg) | Tumor growth inhibition (%) |
|---|---|---|
| Control group | 1224.78 | - |
| Crystalline form I group | 138.33 | 88.70 |

From the above results, it can be seen that the crystalline form I prepared by the present invention has a tumor growth inhibition up to 88.7%. It is suggested that the specific crystalline form further improves the therapeutic activity of the compound. Presumably, the reason may be that the crystalline form I greatly reduces the impurities which are unfavorable to the activity or harmful, and features good solvent compatibility at administration, thereby facilitating absorption of the preparation.

Test Example 3. Inhibition of HBV by Crystalline Form I

Cell plating: HepAD38 cells were seeded in 24-well plates at a density of $8 \times 10^4$ cells/well, each well containing 500 µL of culture medium. Treatment: 9 h after plating, the cells were observed. When the cells were adhered to the wall, drugs (crystalline form I or ETV (entecavir)) at final concentrations of 0.5, 1, 5, 20 and 50 µM were added. The cells were cultured for 48 h, washed with PBS twice, added with the above drugs, and cultured for another 48 h. After the 48 h, the supernatant was collected, and HBV DNA, HBsAg, and HBeAg in the supernatant were detected. HBV DNA was preferentially determined.

HBV DNA assay in culture supernatant: According to TransGen's Viral Nucleic Acid Extraction kit, the nucleic acid was extracted and by SYBR green qPCR, the viral DNA load was determined.

HBsAg and HBeAg assays in culture supernatant: The assay was time-resolved immunofluorescence (ELISA) according to HBsAg and HBeAg assay kits of PE Corporation.

Procedures for determining HBV DNA, HBV RNA, HBsAg and HBeAg in cell culture supernatant are as follows:

1) A proper amount of cells were plated on a 12-well plate. After 24 h, the medium was replaced by a fresh medium free of double-antibody or FBS. HBV plasmids were transfected using Lipo2000. After 6 h, the medium was replaced by a medium containing double-antibody and 10% FBS for continuous culture.

After 48 h, 1 mL of cell culture supernatant was collected for detecting HBsAg and HBeAg. The cells were washed at least 5 times with PBS. 1 mL of the last PBS washings was collected and used as the baseline for determining whether the plasmids were washed away. Note: when washing the cells, PBS was slowly added into the dish along the wall of the dish without resuspending the cells. The dish was then gently shaken to wash the cells, and the residual PBS was discarded after each washing to minimize the plasmid residues.

The cells were transferred to a larger culture dish, and cultured in a culture medium for 3 days. 1 mL of cell supernatant was collected for detecting HBV DNA and HBV RNA. If the detection was not timely performed, the samples were stored at −20° C.

1 mL of collected cell culture supernatant and the last PBS washings collected at 48 h were centrifuged at 5000 rpm for 5 min. 200 µL of the supernatant after centrifugation was added to 5 µL of DNaseI+5 µL of DNaseI buffer, well mixed and subjected to instantaneous centrifugation. The supernatant was incubated for 1 h at 37° C., mixed once every 30 min, and subjected to instantaneous centrifugation. After 1 h, 5 µL of EDTA was added and the system was incubated at 65° C. for 10 min before the DNaseI reaction was terminated.

200 µL of HBV nucleic acid in cell supernatant was concentrated into a system of 20 µL by using a TransGene's HBV nucleic acid extraction kit.

The supernatant HBV DNA level and the baseline level of plasmid in PBS after DNase treatment were measured by real-time PCR. After reverse transcription of HBV RNA into cDNA, real time PCR was performed to detect the level.

(1) HBV DNA quantitative system:

| | |
|---|---|
| $H_2O$ | 9.4 µL |
| HD-F | 1 µL |
| HD-R1 | 1 µL |
| Probe-HD | 0.6 µL |
| 2× probe-MIX | 15 µL |
| In total | 27 µL (gently mixed, instantaneous centrifugation) |
| DNA template | 3 µL |

HD-F:
(SEQ ID NO: 1)
5-CGGCGTTTTATCATMTTCCTCT-3

HD-R1:
(SEQ ID NO: 2)
5-GACAAACGGGCAACATACCTT-3

Probe-HD:
(SEQ ID NO: 3)
VIC-CATCCTGCTGCTATGCCTCATCTTCTT-BHQ1

The primer position was 386-476 in S region (2) cDNA quantitative system after reverse transcription of HBV RNA:

| | |
|---|---|
| H$_2$O | 9.4 μL |
| HR-F2 | 1 μL |
| HR-R2 | 1 μL |
| Probe-HR | 0.6 μL |
| 2× probe-MIX | 15 μL |
| In total | 27 μL (gently mixed, instantaneous centrifugation) |
| cDNA template | 3 μL |

HR-F2:
(SEQ ID NO: 4)
5-AGACCACCAAATGCCCCT-3

HR-R2:
(SEQ ID NO: 5)
5-TCACACCGTAACACACGACAC-3

HR-RT:
(SEQ ID NO: 6)
5-TCTCACACCGTAACACACGACACAGGCGAGGGAGTTCTTCTTCTA-3

Probe-HR
(SEQ ID NO: 7)
FAM-5-CAACACTTCCGGARACTACTGTTGTTAGACG-3-BHQ1

| The quantitative primer sequence was designed in the preC/C region (2297-2287) | Crystalline form I (0.5 μM) | Crystalline form I (1.0 μM) | Crystalline form I (5.0 μM) | ETV (entecavir) |
|---|---|---|---|---|
| Supernatant HBV DVA level | 62% | 63% | 70% | 80% |
| Supernatant HBV RNA level | 48% | 42% | 43% | NA |
| Supernatant HBeAg level | 22% | 17% | 43.1% | 36.8% |

The crystalline form I has good inhibition effect on HBV DNA and supernatant HBeAg. Thus, the crystalline form I can more effectively treat the HBV-induced liver cancer.

Test Example 4

Test Drug: Crystalline Form Prepared in Example 1

Animals: Balb/c inbred mice, male, six weeks old, purchased from Peking University, Health Science Center, Department of Laboratory Animal Science, with license number SCXK(Jing)2016-0010. The breeding environment was clean. The accommodation temperature was 25±2° C. The mice were bred in 12-hour light/darkness cycle, and had sufficient food and water supply.
Related Solution Preparation for Animal Studies:
Preparation of CMC-Na Solution

| | |
|---|---|
| CMC-Na | 5 mg |
| Deionized water | 1000 ml |

The mixture was stirred at a high speed. The CMC-Na initially formed a cotton-like solid, and was gradually dissolved after stirring to give a solution used as a solvent.

Preparation of Crystalline Form I (BS) Solution

| Group | Weight of crystalline form I(BS) (mg) | Solvent and volume |
|---|---|---|
| Model group | 0 | 5‰ CMC-Na, 5 ml |
| BSL group | 90 | 5‰ CMC-Na, 5 ml |
| BSM group | 180 | 5‰ CMC-Na, 5 ml |

After being prepared into a solution or suspension, the compound was administered to the mice at a dose of 5 mL/Kg.
Preparation of 25% CCl$_4$ Solution

| | |
|---|---|
| CCl$_4$ | 10 ml |
| Olive oil | 40 ml |

The mixture was stirred at a high speed and preserved at room temperature after being well mixed.

Materials

BS1801 (Peking University, School of Pharmaceutical Sciences), mHSC cell line (BeNa Culture Collection, Hebei, China), AML12 cell line, fetal bovine serum (Gibco), DMEM medium (M&C), F12 medium, TGF-β1 (Novoprotein), cell culture factor mixture (Sigma), dexamethasone (Solarbio), carbon tetrachloride (Beijing Ouhe Technology Co., Ltd.), olive oil (Macklin), sulforhodamine B (Sigma), paraformaldehyde (Yuanye), Tris (Ameresco), sodium carboxymethylcellulose (CMC-Na) and animal tissue fixative.

Procedures

1. Cell Culture and Cell Viability Assay

Mouse hepatic stellate mHSC cells were cultured using 20% FBS in an oven at 37° C., 5% CO$_2$. In the cell proliferation experiment, the cell density was 5000 cells/well, treatment was given after induction with 5 ng/mL TGF-β1 for 24 h, and the cell proliferation inhibition was detected by SRB.

2. Immunoblotting

The mHSC cells were transferred to dishes at 10$^6$ cells/dish and treated 12 h after adhesion. After 48 h, cells in the supernatant were collected, and combined with adherent cells. The cells were lysed on ice for 30 min using an RIPA lysate containing protease inhibitor and centrifuged at 16000 rpm for 15 min, and the supernatant was retained. The concentration of cell lysate was determined by BCA, and a certain amount of loading buffer was added to prepare a protein sample with a concentration of 2.5 μg/μL. The content of the α-SMA, the Collagen I and the Collagen III was determined by SDS-PAGE.

Figure 6:
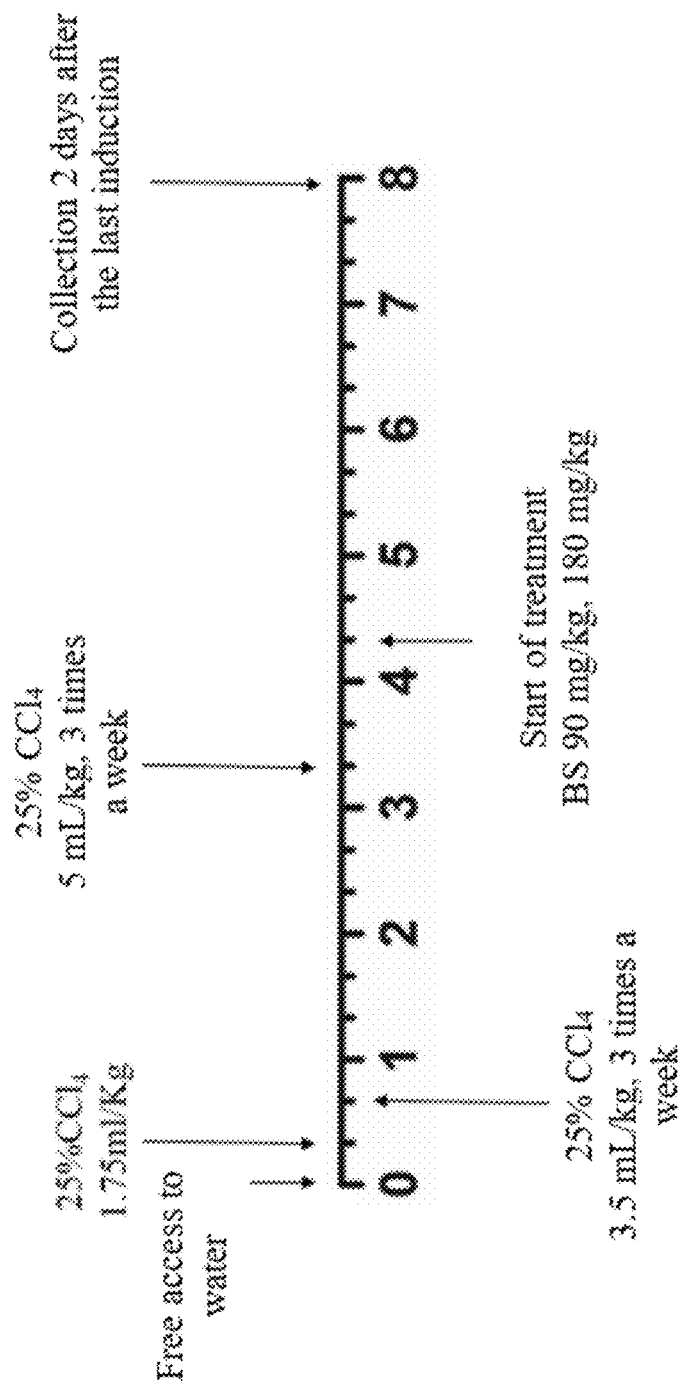
FIG. 6 illustrates the animal model in Test Example 4.

3. Animal Study 20 male Balb/c mice aged 6 weeks were randomized into 4 groups. After a staged gradient induction using 25% CCl$_4$ for 4 weeks (three times a week), the treatment started in the BSL (90 mg/kg) group and the BSM (180 mg/kg) group once a day, and the control group and model group were administered with 5‰ CMC-Na solution. After 8 weeks of induction, the mice were sacrificed and the blood was collected and centrifuged at 3000 rpm for 15 min to give the serum for detecting TGF-β1, TrxR1, AST, ALT, ALP, TP and the expression (hepatic fibrosis animal model is shown in FIG. 6). Part of liver was fixed with 4% paraformaldehyde, and subjected to immunohistochemical HE staining and Masson staining. Expressions of α-SMA and Collagen I in liver tissue were detected immunohistochemically. Part of liver was preserved in liquid nitrogen.

Figure 7:
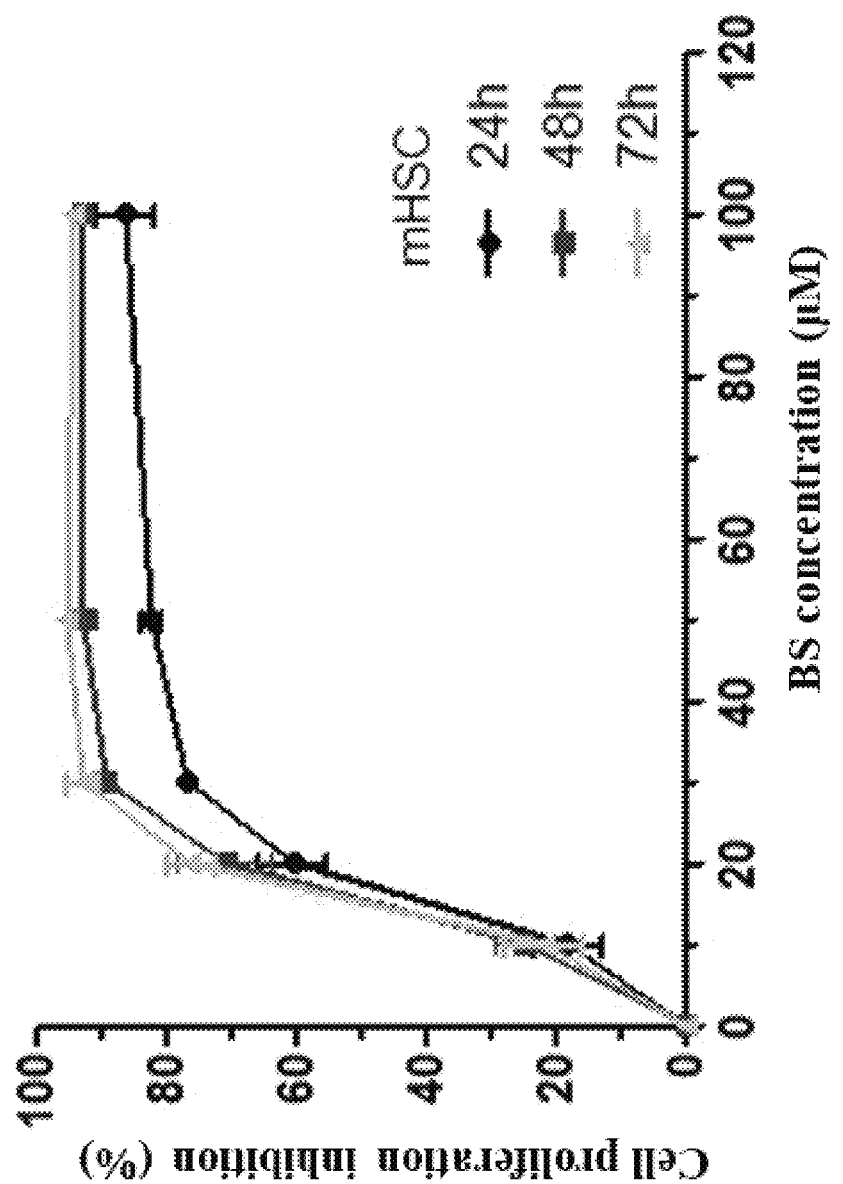
FIG. 7 illustrates the HSC cell growth inhibition (%) by different concentrations of the crystalline form I.

FIG. 7 illustrates the measured $IC_{50}$ values, and it can be seen from the result in FIG. 7 that, since TGF β1 plays a very important pathological role in fibrotic lesions and HSC consists of 5% of normal liver cells, liver injury usually leads to HSC transformation and activation, wherein TGF β1 is a potent fibrosis factor. The inhibitory effect of HSC by the crystalline form of the present invention is one of important targets for anti-fibrosis effect.

Figure 8:
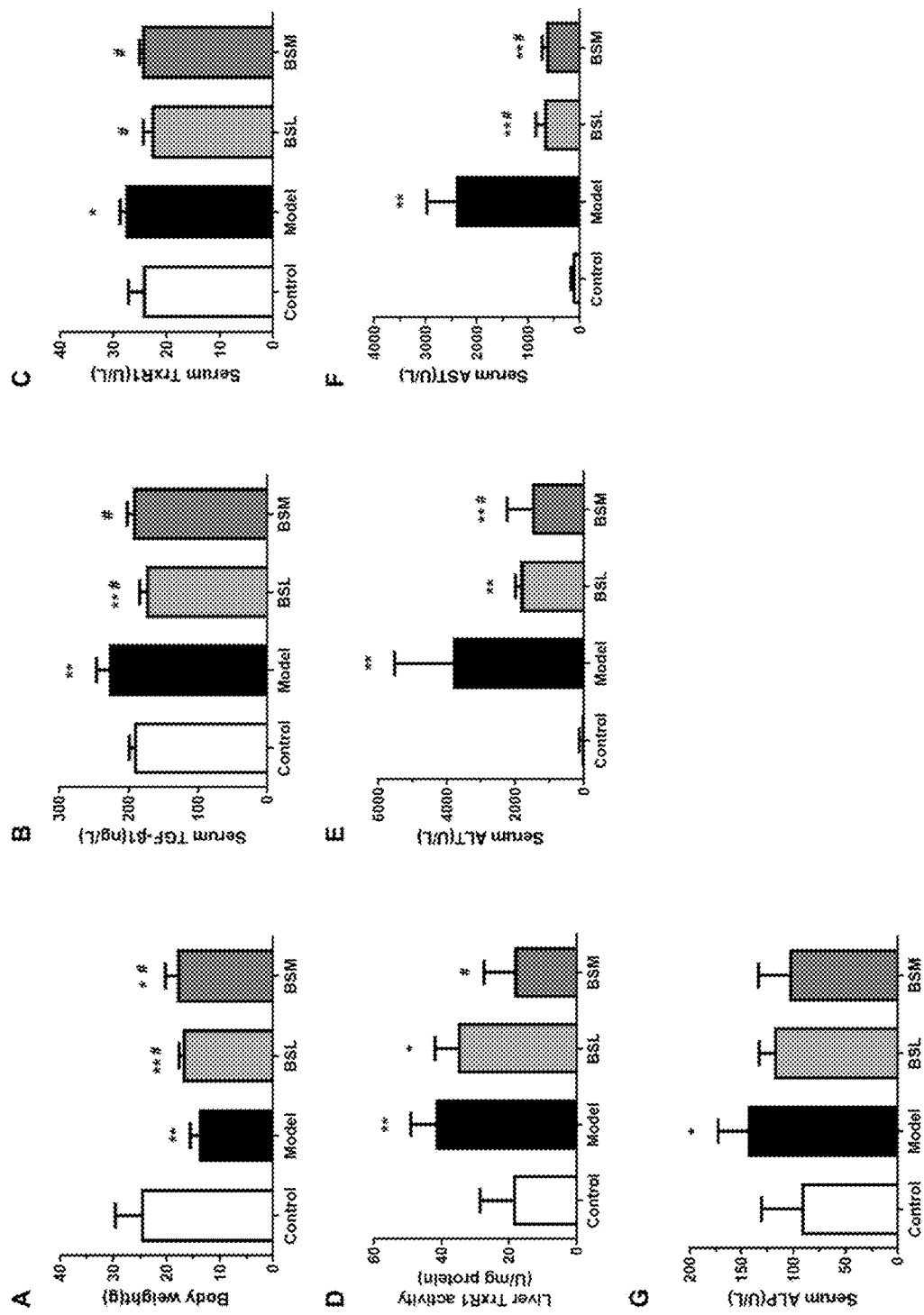
FIG. 8 illustrates the effect of different concentrations of the crystalline form I on body weight (A), hepatic biochemical indicators (E, F, and G), TR activity (C and D) and TGF levels (B) in hepatic fibrosis animal models.

FIG. 8 is a comparison of various biochemical indicators and important protein markers in serum after the fibrosis model mice were administered with BS (the corresponding results are shown in the following table). As can be seen from FIG. 8 and the results in the following table, the average body weight of the mice in the model group and the treatment groups was significantly reduced, particularly in the model group, as compared to that in the control group. At the end of the study, the average body weights in the four groups were 24.76±4.84 g, 14.08±1.51 g, 17.00±0.68 g and 18.04±2.23 g, respectively.

TABLE 1

Recovery of body weight and serum biochemical indicators in mice of all groups at the end of the study

| Group | Average Body weight | TGF | TrxR1 | ALT | AST | ALP | TP | ALB |
|---|---|---|---|---|---|---|---|---|
| Control group | 24 | 0.84 | 0.88 | 0.02 | 0.06 | 0.64 | 1.11 | 1.13 |
| Model group | 14 | 1.00 | 1.00 | 1.00 | 1.00 | 1.00 | 1.00 | 1.00 |
| BSL | 17 | 0.76 | 0.82 | 0.48 | 0.29 | 0.82 | 1.35 | 1.83 |
| BSM | 18 | 0.85 | 0.89 | 0.39 | 0.27 | 0.73 | 1.36 | 1.47 | n ≥ 4

Figure 9:
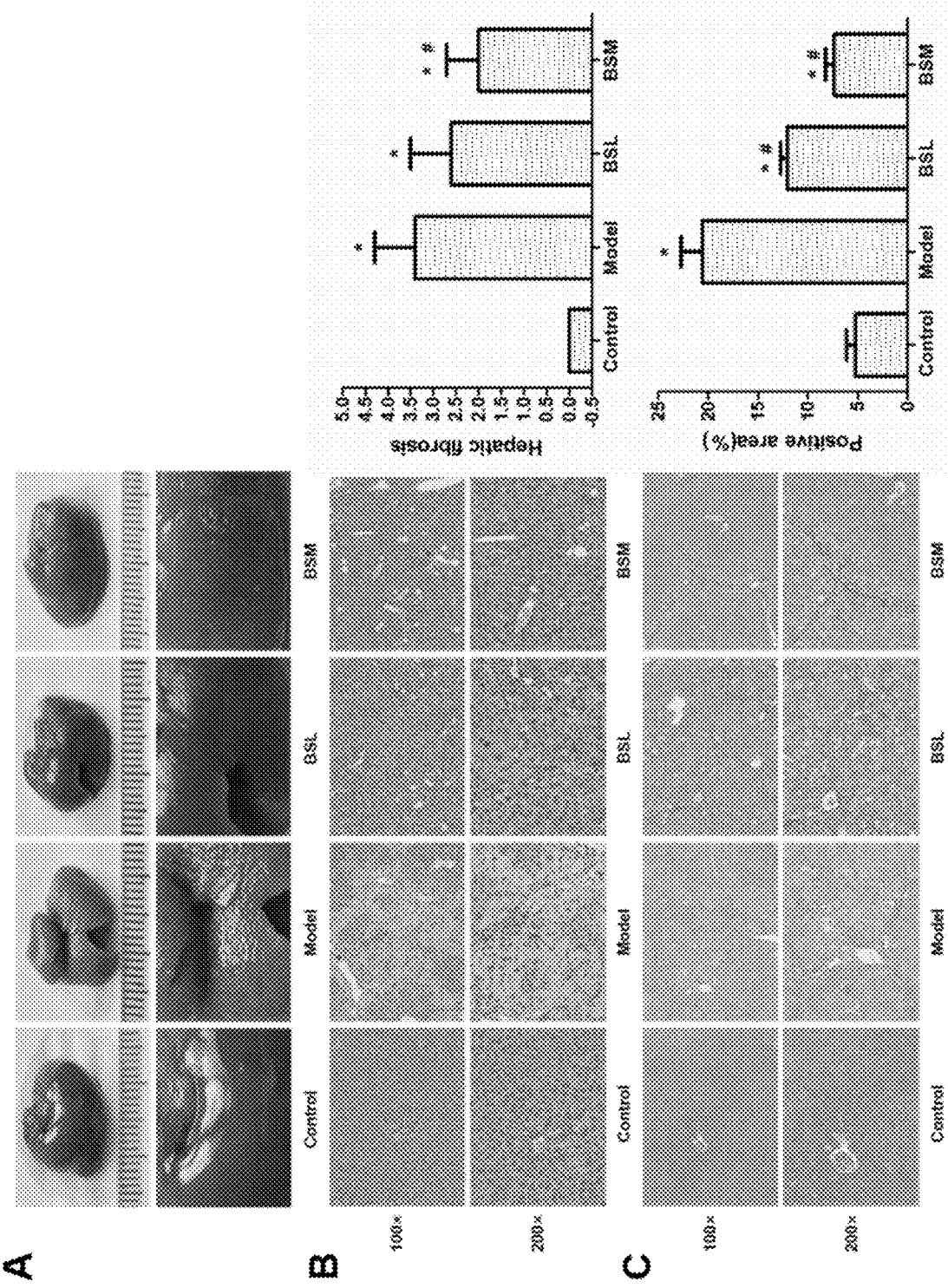
FIG. 9 illustrates the roughness of liver surface (A), HE staining (B) and Masson staining (C) for different concentrations of the crystalline form I in hepatic fibrosis animal models.

FIG. 9 shows the results of immunohistochemical staining in livers and tissues after intervention in control, model, BS low dose (BSL) and BS medium dose (BSM) groups. As can be seen from the results of group A, the mice in the control group demonstrated smooth, glossy, dark red, soft liver surface, indicating a normal liver status. At the end of the study, the mice in the model group showed decreased activity, a weight loss up to 43.2%, a frosted, light-colored, hard and granular surface, and a fibroid status, indicating that a successful model establishment. Such symptoms in livers of the mice in the treatment groups were improved, and the granular sensation on the liver surface was relieved.

The HE staining results show that the liver cells demonstrated severe edema and severe inflammation in the model group as compared with the control group, and most of the liver cell boundary plates were destroyed (>50%); in contrast, in the BSL and BSM groups, symptoms of hepatocyte necrosis and inflammation were significantly reduced as compared to the model group. Masson staining results show that the mice in the model group demonstrated bridging fibrosis between portal areas, and fibrous intervals were formed; the BSL group and the BSM group showed gradually relieved symptoms as compared with the model group; the control group only demonstrated a few fibers around the portal area.

Figure 10:
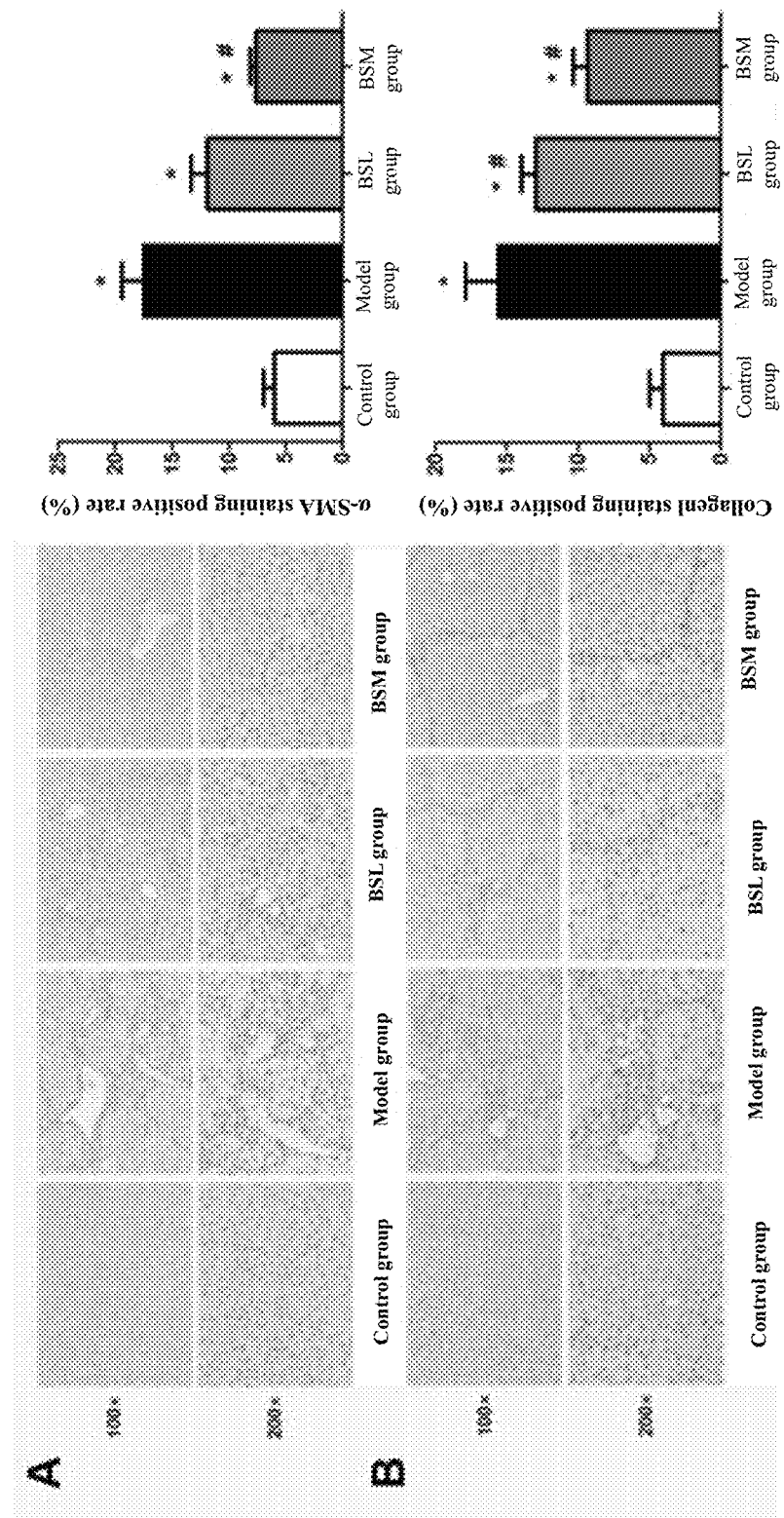
FIG. 10 illustrates the expression of (A) α-SMA and (B) Collagen1A1 in liver in various groups of mice at the end of the hepatic fibrosis model experiment at different concentrations of the crystalline form I.

FIG. 10 illustrates the expression of (A) α-SMA and (B) Collagen1A1 in liver in various groups of mice at the end of the hepatic fibrosis model experiment at different concentrations of the crystalline form I. In FIG. 10, the results of α-SMA staining and Collagen1 staining suggest that the expression level of corresponding proteins in liver of mice in the model group was significantly increased as compared with the control group, while the symptoms of the BSL group and the BSM group were significantly reduced, showing significant differences from the model group and the control group.

In summary, the present invention provides a crystalline form I of the 1,4-BIS[1,2-BENZISOSELENAZOL-3(2H)-one]-butane. The crystalline form I has good stability, is beneficial to the preparation, use, shipping and preservation of pharmaceutical compositions and preparations, and fully ensures the safety of medication and the quality of medicaments.

In addition, the crystalline form features high solubility, reasonable bioavailability, low toxicity and excellent tumor inhibitory activity, particularly overall inhibition in liver cancer patients carrying HBV and functional inhibition effects in the hepatic fibrosis process and core fibrosis, tumorigenesis and tumor growth. Thus the crystalline form has the protective function for the whole process from HBV to liver cancer.

Finally, the preparation method of the crystalline form I disclosed herein features the advantages of ease-to-operate, good reproducibility, high yield and suitability for industrial production, thus having great application value.

The examples of the present invention have been described above. However, the present invention is not limited to the above examples. Any modification, equivalent, improvement and the like made without departing from the spirit and principle of the present invention shall fall within the protection scope of the present invention.

The invention claimed is:

1. A crystalline form of 1,4-BIS[1,2-BENZISOSELENA-ZOL-3(2H)-one]-butane is a crystalline form I, wherein the crystalline form I has characteristic peaks at 2θ angles of 6.15±0.20°, 12.28±0.20°, 18.44±0.20°, 19.09±0.20°, 22.20±0.20°, 23.68±0.20°, 25.92±0.20°, 27.50±0.20°, 30.95±0.20°, and 32.45±0.20° by X-ray powder diffraction using Cu-Kα radiation.

2. The crystalline form I according to claim 1 having characteristic peaks at 2θ angles of 6.15±0.20°, 12.28±0.20°, 18.44±0.20°, 19.09±0.20°, 21.89±0.20°, 22.20±0.20°, 23.68±0.20°, 25.92±0.20°, 27.50±0.20°, 30.95±0.20°, 32.45±0.20°, 35.79±0.20°, 37.37±0.20°, and 37.72±0.20° by X-ray powder diffraction using Cu-Kα radiation.

3. The crystalline form I according to claim 1 having an XRD pattern shown in FIG. 1, or is equivalent to a crystalline form corresponding to the XRD pattern.

4. A crystalline form of 1,4-BIS[1,2-BENZISOSELENA-ZOL-3(2H)-one]-butane is a crystalline form I, wherein the crystalline form I is a monocrystal having the following monocrystalline properties,

| | |
|---|---|
| System | monoclinic |
| Space group | P21/a |
| a (Å) | 12.000 (1) |
| b (Å) | 4.921 (1) |
| c (Å) | 14.591 (1) |
| β (°) | 97.61 (1). |

5. A method for preparing the crystalline form I according to claim 1, comprising:
dissolving 1,4-BIS[1,2-BENZISOSELENAZOL-3(2H)-one]-butane in a solvent S1, and adding an antisolvent S2 to give the crystalline form I;
wherein the solvent S1 is selected from dimethyl sulfoxide (DMSO) and a mixture of 1-10% acetone or tetrahydrofuran (v/v) in DMSO;
the antisolvent S2 is selected from water, acetonitrile, methyl tert-butyl ether (MTBE), isopropyl acetate, methanol and ethyl acetate, provided that when the solvent S1 is DMSO, the solvent S2 is not ethyl acetate.

6. A method for inhibiting activities of gelatinase-2 and the gelatinase-9, comprising administering a medicament comprising the crystalline form I according to claim 1 to a subject in need thereof.

7. A method for treating hepatitis B or liver cancer, comprising administering a medicament comprising the crystalline form I according to claim 1, wherein the liver cancer is HBV-associated liver cancer.

8. A pharmaceutical composition, comprising the crystalline form I according to claim 1.

9. A method for preparing the crystalline form I according to claim 4, comprising:
dissolving 1,4-BIS[1,2-BENZISOSELENAZOL-3(2H)-one]-butane in a solvent S1, and adding an antisolvent S2 to obtain the crystalline form I,
wherein the solvent S1 is selected from dimethyl sulfoxide (DMSO) and a mixture of 1-10% acetone or tetrahydrofuran (v/v) in DMSO, and
the solvent S2 is selected from water, acetonitrile, methyl tert-butyl ether (MTBE), isopropyl acetate, methanol and ethyl acetate, provided that when the solvent S1 is DMSO, the solvent S2 is not ethyl acetate.

10. A method for inhibiting activities of gelatinase-2 and the gelatinase-9, comprising administering a medicament comprising the crystalline form I according to claim 4 to a subject in need thereof.

11. A method for treating hepatitis B or liver cancer, comprising administering a medicament comprising the crystalline form I according to claim 4 to a subject in need thereof, wherein the liver cancer is HBV-associated liver cancer.

12. A pharmaceutical composition, comprising the crystalline form I according to claim 4.

13. A method for treating an immune injury disease or an immune regulation function-dependent or -promoted relevant disease, comprising administering a medicament comprising the crystalline form I according to claim 1 to a subject in need thereof, wherein the immune injury disease and the immune regulation function-dependent or -promoted relevant disease are selected from viral hepatitis, allergic diseases, and acquired immunodeficiency syndrome.

14. A method for treating an immune injury disease or an immune regulation function-dependent or -promoted relevant disease, comprising administering a medicament comprising the crystalline form I according to claim 4 to a subject in need thereof, wherein the immune injury disease and the immune regulation function-dependent or -promoted relevant disease are selected from viral hepatitis, allergic diseases, and acquired immunodeficiency syndrome.

15. A method for treating hepatic fibrosis, comprising administering a medicament comprising the crystalline form I according to claim 1 to a subject in need thereof.

16. A method for treating hepatic fibrosis, comprising administering a medicament comprising the crystalline form I according to claim 4 to a subject in need thereof.

* * * * *

SEQUENCE LISTING

<160> NUMBER OF SEQ ID NOS: 7

<210> SEQ ID NO 1
<211> LENGTH: 22
<212> TYPE: DNA
<213> ORGANISM: artificial sequence
<220> FEATURE:
<223> OTHER INFORMATION: synthesized

<400> SEQUENCE: 1
cggcgtttta tcatmttcct ct                                              22

```
<210> SEQ ID NO 2
<211> LENGTH: 21
<212> TYPE: DNA
<213> ORGANISM: artificial sequence
<220> FEATURE:
<223> OTHER INFORMATION: synthesized

<400> SEQUENCE: 2
gacaaacggg caacatacct t                                      21

<210> SEQ ID NO 3
<211> LENGTH: 27
<212> TYPE: DNA
<213> ORGANISM: artificial sequence
<220> FEATURE:
<223> OTHER INFORMATION: synthesized

<400> SEQUENCE: 3
catcctgctg ctatgcctca tcttctt                                27

<210> SEQ ID NO 4
<211> LENGTH: 18
<212> TYPE: DNA
<213> ORGANISM: artificial sequence
<220> FEATURE:
<223> OTHER INFORMATION: synthesized

<400> SEQUENCE: 4
agaccaccaa atgcccct                                          18

<210> SEQ ID NO 5
<211> LENGTH: 21
<212> TYPE: DNA
<213> ORGANISM: artificial sequence
<220> FEATURE:
<223> OTHER INFORMATION: synthesized

<400> SEQUENCE: 5
tcacaccgta acacacgaca c                                      21

<210> SEQ ID NO 6
<211> LENGTH: 45
<212> TYPE: DNA
<213> ORGANISM: artificial sequence
<220> FEATURE:
<223> OTHER INFORMATION: synthesized

<400> SEQUENCE: 6
tctcacaccg taacacacga cacaggcgag ggagttcttc ttcta             45

<210> SEQ ID NO 7
<211> LENGTH: 31
<212> TYPE: DNA
<213> ORGANISM: artificial sequence
<220> FEATURE:
<223> OTHER INFORMATION: synthesized

<400> SEQUENCE: 7
caacacttcc ggaractact gttgttagac g                           31
```